United States Patent
Horn et al.

(10) Patent No.: US 8,296,162 B1
(45) Date of Patent: Oct. 23, 2012

(54) SYSTEMS, DEVICES, AND METHODS FOR PROVIDING HEALTHCARE INFORMATION

(75) Inventors: Alan Horn, Chicago, IL (US); Ann Mond Johnson, River Forest, IL (US); Joe Donlan, Chicago, IL (US); Tracy Heilman, Chicago, IL (US); John Fiacco, Alpharetta, GA (US)

(73) Assignee: WebMD LLC., New York, NY (US)

(*) Notice: Subject to any disclaimer, the term of this patent is extended or adjusted under 35 U.S.C. 154(b) by 1327 days.

(21) Appl. No.: 11/344,628

(22) Filed: Feb. 1, 2006

Related U.S. Application Data

(60) Provisional application No. 60/648,821, filed on Feb. 1, 2005.

(51) Int. Cl.
*G06Q 10/00* (2012.01)
*G06Q 50/00* (2012.01)

(52) U.S. Cl. ................................. 705/2; 705/3
(58) Field of Classification Search .............. 705/2–4
See application file for complete search history.

(56) References Cited

U.S. PATENT DOCUMENTS

| | | | |
|---|---|---|---|
| 4,315,309 A | 2/1982 | Coli | |
| 4,622,013 A | 11/1986 | Cerchio | |
| 4,766,542 A | 8/1988 | Pilarczyk | |
| 4,783,917 A | 11/1988 | Smith et al. | |
| 4,812,994 A | 3/1989 | Taylor et al. | |
| 4,816,653 A | 3/1989 | Anderl et al. | |
| 4,839,822 A | 6/1989 | Dormond et al. | |
| 4,847,764 A | 7/1989 | Halvorson | |
| 4,858,121 A | 8/1989 | Barber et al. | |
| 4,868,376 A | 9/1989 | Lessin et al. | |
| 4,882,474 A | 11/1989 | Anderl et al. | |
| 4,916,611 A | 4/1990 | Doyle, Jr. et al. | |
| 4,949,251 A | 8/1990 | Griffin et al. | |
| 4,960,982 A | 10/1990 | Takahira | |
| 4,984,272 A | 1/1991 | McIlroy et al. | |
| 5,018,067 A | 5/1991 | Mohlenbrock et al. | |
| 5,072,383 A | 12/1991 | Brimm et al. | |
| 5,077,666 A | 12/1991 | Brimm et al. | |
| 5,103,498 A | 4/1992 | Lanier et al. | |
| 5,136,502 A | 8/1992 | Van Remortel et al. | |
| 5,150,409 A | 9/1992 | Elsner | |

(Continued)

FOREIGN PATENT DOCUMENTS

WO    WO-9512812 A1    5/1995

(Continued)

OTHER PUBLICATIONS

Subimo Website found at www.archive.org for various dates from 2001 to 2004.*

(Continued)

*Primary Examiner* — Luke Gilligan
*Assistant Examiner* — Joseph Burgess
(74) *Attorney, Agent, or Firm* — Wilmer Cutler Pickering Hale & Dorr LLP

(57) ABSTRACT

Certain exemplary embodiments can comprise a method that can comprise, for a predetermined user, automatically determining a score for each resource from a plurality of predetermined resources based on the user's weighting of predetermined factors associated with the resources and an objective score for each factor for each resource, ranking the scored resources, and/or providing an identity of a best matched resource for the user.

12 Claims, 3 Drawing Sheets

U.S. PATENT DOCUMENTS

| | | |
|---|---|---|
| 5,239,617 A | 8/1993 | Gardner et al. |
| 5,241,671 A | 8/1993 | Reed et al. |
| 5,251,152 A | 10/1993 | Notess |
| 5,267,155 A | 11/1993 | Buchanan et al. |
| 5,277,188 A | 1/1994 | Selker |
| 5,291,399 A | 3/1994 | Chaco |
| 5,299,121 A | 3/1994 | Brill et al. |
| 5,301,105 A | 4/1994 | Cummings, Jr. |
| 5,301,246 A | 4/1994 | Archibald et al. |
| 5,301,319 A | 4/1994 | Thurman et al. |
| 5,324,718 A | 6/1994 | Loftsson |
| 5,325,294 A | 6/1994 | Keene |
| 5,325,478 A | 6/1994 | Shelton et al. |
| 5,327,341 A | 7/1994 | Whalen et al. |
| 5,337,919 A | 8/1994 | Spaulding et al. |
| 5,410,704 A | 4/1995 | Norden-Paul et al. |
| 5,430,875 A | 7/1995 | Ma |
| 5,459,536 A | 10/1995 | Shalon et al. |
| 5,465,082 A | 11/1995 | Chaco |
| 5,468,110 A | 11/1995 | McDonald et al. |
| 5,471,382 A | 11/1995 | Tallman et al. |
| 5,472,954 A | 12/1995 | Loftsson |
| 5,477,447 A | 12/1995 | Luciw et al. |
| 5,485,544 A | 1/1996 | Nonaka et al. |
| 5,491,800 A | 2/1996 | Goldsmith et al. |
| 5,502,944 A | 4/1996 | Kraft et al. |
| 5,517,405 A | 5/1996 | McAndrew et al. |
| 5,519,607 A | 5/1996 | Tawil |
| 5,526,482 A | 6/1996 | Stallmo et al. |
| 5,542,420 A | 8/1996 | Goldman et al. |
| 5,546,472 A | 8/1996 | Levin |
| 5,550,971 A | 8/1996 | Brunner et al. |
| 5,552,586 A | 9/1996 | Kalman |
| 5,558,638 A | 9/1996 | Evers et al. |
| 5,559,885 A | 9/1996 | Drexler et al. |
| 5,559,888 A | 9/1996 | Jain et al. |
| 5,560,008 A | 9/1996 | Johnson et al. |
| 5,560,011 A | 9/1996 | Uyama |
| 5,572,422 A | 11/1996 | Nematbakhsh et al. |
| 5,576,954 A | 11/1996 | Driscoll |
| 5,583,831 A | 12/1996 | Churchill et al. |
| 5,588,148 A | 12/1996 | Landis et al. |
| 5,590,038 A | 12/1996 | Pitroda |
| 5,593,267 A | 1/1997 | McDonald et al. |
| 5,594,786 A | 1/1997 | Chaco et al. |
| 5,596,994 A | 1/1997 | Bro |
| 5,597,995 A | 1/1997 | Williams et al. |
| 5,612,869 A | 3/1997 | Letzt et al. |
| 5,613,106 A | 3/1997 | Thurman et al. |
| 5,619,991 A | 4/1997 | Sloane |
| 5,623,242 A | 4/1997 | Dawson, Jr. et al. |
| 5,629,981 A | 5/1997 | Nerlikar |
| 5,633,368 A | 5/1997 | Hirsenkorn |
| 5,664,109 A | 9/1997 | Johnson et al. |
| 5,664,207 A | 9/1997 | Crumpler et al. |
| 5,666,492 A | 9/1997 | Rhodes et al. |
| 5,671,362 A | 9/1997 | Cowe et al. |
| 5,672,154 A | 9/1997 | Sillen et al. |
| 5,682,142 A | 10/1997 | Loosmore et al. |
| 5,689,229 A | 11/1997 | Chaco et al. |
| 5,689,247 A | 11/1997 | Welner |
| 5,692,125 A | 11/1997 | Schloss et al. |
| 5,694,806 A | 12/1997 | Martin et al. |
| 5,700,998 A | 12/1997 | Palti |
| 5,704,044 A | 12/1997 | Tarter et al. |
| 5,704,371 A | 1/1998 | Shepard |
| 5,706,431 A | 1/1998 | Otto |
| 5,710,551 A | 1/1998 | Ridgeway |
| 5,713,485 A | 2/1998 | Liff et al. |
| 5,735,105 A | 4/1998 | Stroud et al. |
| 5,736,580 A | 4/1998 | Huntington et al. |
| 5,737,396 A | 4/1998 | Garcia |
| 5,737,539 A | 4/1998 | Edelson et al. |
| 5,742,816 A | 4/1998 | Barr et al. |
| 5,745,366 A | 4/1998 | Higham et al. |
| 5,754,111 A | 5/1998 | Garcia |
| 5,759,095 A | 6/1998 | De Weerd |
| 5,764,923 A | 6/1998 | Tallman et al. |
| 5,772,585 A | 6/1998 | Lavin et al. |
| 5,776,783 A | 7/1998 | Kell |
| 5,778,225 A | 7/1998 | Supernaw-Issen et al. |
| 5,781,442 A | 7/1998 | Engleson et al. |
| 5,784,635 A | 7/1998 | McCallum |
| 5,790,409 A | 8/1998 | Fedor et al. |
| 5,790,785 A | 8/1998 | Klug et al. |
| 5,797,515 A | 8/1998 | Liff et al. |
| 5,799,292 A | 8/1998 | Hekmatpour |
| 5,799,981 A | 9/1998 | Tung et al. |
| 5,803,498 A | 9/1998 | Tung et al. |
| 5,805,454 A | 9/1998 | Valerino, Sr. et al. |
| 5,805,676 A | 9/1998 | Martino |
| 5,809,476 A | 9/1998 | Ryan |
| 5,812,410 A | 9/1998 | Lion et al. |
| 5,815,665 A | 9/1998 | Teper et al. |
| 5,822,544 A | 10/1998 | Chaco et al. |
| 5,823,948 A | 10/1998 | Ross, Jr. et al. |
| 5,823,949 A | 10/1998 | Goltra |
| 5,827,180 A | 10/1998 | Goodman |
| 5,832,449 A | 11/1998 | Cunningham |
| 5,832,450 A | 11/1998 | Myers et al. |
| 5,832,488 A | 11/1998 | Eberhardt |
| 5,833,599 A | 11/1998 | Schrier et al. |
| 5,835,897 A | 11/1998 | Dang |
| 5,835,900 A | 11/1998 | Fagg, III et al. |
| 5,836,312 A | 11/1998 | Moore |
| 5,841,970 A | 11/1998 | Tabuki |
| 5,845,255 A | 12/1998 | Mayaud |
| 5,845,264 A | 12/1998 | Nellhaus |
| 5,848,397 A | 12/1998 | Marsh et al. |
| 5,857,190 A | 1/1999 | Brown |
| 5,857,967 A | 1/1999 | Frid et al. |
| 5,862,327 A | 1/1999 | Kwang et al. |
| 5,867,821 A | 2/1999 | Ballantyne et al. |
| 5,903,889 A | 5/1999 | de la Huerga et al. |
| 5,905,884 A | 5/1999 | Williams |
| 5,915,240 A | 6/1999 | Karpf |
| 5,926,811 A | 7/1999 | Miller et al. |
| 5,937,387 A | 8/1999 | Summerell et al. |
| 5,950,630 A | 9/1999 | Portwood et al. |
| 5,953,704 A | 9/1999 | McIlroy et al. |
| 5,960,403 A | 9/1999 | Brown |
| 5,967,789 A | 10/1999 | Segel et al. |
| 5,974,412 A | 10/1999 | Hazlehurst et al. |
| 5,978,842 A | 11/1999 | Noble et al. |
| 5,996,715 A | 12/1999 | Peay et al. |
| 6,003,020 A | 12/1999 | Hazlehurst et al. |
| 6,006,269 A | 12/1999 | Phaal |
| 6,018,619 A | 1/2000 | Allard et al. |
| 6,031,818 A | 2/2000 | Lo et al. |
| 6,039,688 A | 3/2000 | Douglas et al. |
| 6,047,327 A | 4/2000 | Tso et al. |
| 6,061,657 A | 5/2000 | Whiting-O'Keefe |
| 6,070,160 A | 5/2000 | Geary |
| 6,073,106 A | 6/2000 | Rozen et al. |
| 6,073,163 A | 6/2000 | Clark et al. |
| 6,076,166 A | 6/2000 | Moshfeghi et al. |
| 6,092,196 A | 7/2000 | Reiche |
| 6,112,183 A | 8/2000 | Swanson et al. |
| 6,141,759 A | 10/2000 | Braddy |
| 6,167,523 A | 12/2000 | Strong |
| 6,178,416 B1 | 1/2001 | Thompson et al. |
| 6,189,036 B1 | 2/2001 | Kao |
| 6,219,674 B1 | 4/2001 | Classen |
| 6,253,228 B1 | 6/2001 | Ferris et al. |
| 6,263,330 B1 | 7/2001 | Bessette |
| 6,272,468 B1 | 8/2001 | Melrose |
| 6,289,535 B1 | 9/2001 | Hernandez |
| 6,292,796 B1 | 9/2001 | Drucker et al. |
| 6,334,778 B1 | 1/2002 | Brown |
| 6,347,374 B1 | 2/2002 | Drake et al. |
| 6,362,836 B1 | 3/2002 | Shaw et al. |
| 6,366,956 B1 | 4/2002 | Krishnan |
| 6,385,611 B1 | 5/2002 | Cardona |
| 6,401,072 B1 | 6/2002 | Haudenschild et al. |
| 6,449,598 B1 | 9/2002 | Green et al. |
| 6,505,196 B2 | 1/2003 | Drucker et al. |
| 6,581,038 B1 | 6/2003 | Mahran |

| | | | |
|---|---|---|---|
| 6,584,445 | B2 | 6/2003 | Papageorge |
| 6,671,282 | B1 | 12/2003 | Haapalehto et al. |
| 6,738,754 | B1 | 5/2004 | Norman, Jr. |
| 6,826,696 | B1 | 11/2004 | Chawla et al. |
| 6,904,408 | B1 | 6/2005 | McCarthy et al. |
| 7,020,618 | B1 | 3/2006 | Ward |
| 2001/0021910 | A1 | 9/2001 | Goldstein |
| 2002/0035529 | A1 | 3/2002 | Tooke |
| 2002/0138325 | A1 | 9/2002 | Mashimo et al. |
| 2002/0147617 | A1 | 10/2002 | Schoenbaum et al. |
| 2002/0165737 | A1 | 11/2002 | Mahran |
| 2003/0046113 | A1 | 3/2003 | Johnson et al. |
| 2003/0163349 | A1* | 8/2003 | Ho ................................. 705/2 |
| 2003/0167187 | A1* | 9/2003 | Bua ................................ 705/2 |
| 2004/0010426 | A1 | 1/2004 | Berdou |
| 2004/0039667 | A1 | 2/2004 | Winklevoss et al. |
| 2004/0044548 | A1 | 3/2004 | Marshall et al. |
| 2004/0088362 | A1 | 5/2004 | Curbow et al. |
| 2005/0004983 | A1 | 1/2005 | Boyd |
| 2005/0010446 | A1 | 1/2005 | Lash et al. |
| 2005/0060209 | A1 | 3/2005 | Hill et al. |
| 2005/0108067 | A1 | 5/2005 | Chapman et al. |
| 2005/0251428 | A1 | 11/2005 | Dust et al. |
| 2006/0004607 | A1 | 1/2006 | Marshall et al. |
| 2006/0026036 | A1 | 2/2006 | Mahmood |
| 2006/0064332 | A1 | 3/2006 | Schoenbaum et al. |
| 2006/0136264 | A1 | 6/2006 | Eaton et al. |
| 2006/0149595 | A1 | 7/2006 | Williams et al. |
| 2006/0161456 | A1* | 7/2006 | Baker et al. ...................... 705/2 |
| 2007/0027727 | A1 | 2/2007 | Cochrane |
| 2007/0043595 | A1 | 2/2007 | Pederson |
| 2008/0010086 | A1 | 1/2008 | Skelly et al. |
| 2008/0021288 | A1 | 1/2008 | Bowman et al. |
| 2008/0027753 | A1 | 1/2008 | Dean |
| 2008/0133272 | A1 | 6/2008 | Marshall |
| 2008/0133290 | A1 | 6/2008 | Siegrist et al. |

FOREIGN PATENT DOCUMENTS

| | | | |
|---|---|---|---|
| WO | WO-0152106 | A2 | 7/2001 |
| WO | WO-0169483 | A2 | 9/2001 |

OTHER PUBLICATIONS

"Insurers Roll Out Hospital Quality Data But Hospital Grades, Cost Info Is Optional", Managed Care Week, Mar. 23, 2003, vol. 13, No. 11, p. 1.*

Fiacco, Joseph, "Subimo's Decision Support System Chosen to Guide the Members of a New Kind of Health Plan", Press Release, Jun. 20, 2001, 2 Pages, Chicago, IL.

Subimo, HeathcareAdvisor™ Website Search, "Topic: Heart Attack" http://web.archive.org/web20041224070851/http:/www.subimo.com/products/comps/hosp_choose.htm, 2004,4 Pages.

Subimo, "FAQ on the Subimo Healthcare Advisor™", Oct. 2005, 4 Pages.

"Introducing CarCalcsm—An Industry First!" BlueCross BlueShield of Florida, Fall 2006 (19 pages).

Anonymous, Apr. 16, 2011, New Product Newsire, Drug Topics; Oradell, Medical Economics Inc. vol. 145, Issue 8, pp. 74-77.

Brown, Dick, "Humana's New Real Time Claims Adjudication Enables Faster Member Payment to Physicians and Calculates Members Exact Portion of Bill," Humana. Jan. 31, 2006 Retrieved from <www.humana.com/corporatecomm/newsroom/releases/PR-news . . . > on Apr. 5, 2007 (3 pages).

Detmer, W.M. et al., "Medweaver: Integrating Decision Support, Literature Searching, and Web Exploration using the UMLS Metathesaurus", 1997. 5 pages.

Family Health Budget—Health Care Savings Account Calculator. Retrieved from <www.familyhealthbudget.com/basics/hsacalculator.asp> on Aug. 8, 2006 (3 pages).

Freeman, M. "What to do when a pharmacist suspects a script is forged," Pulse, London Issue 00486000, (Mar. 31, 2001). 3 pages.

G. Carenini, et al., "An Information-Based Bayesian Approach to History Taking," 5th Conf. on Artificial Intelligence in Medicine Europe, pp. 129-138, Jun. 1995.

Health Savings Account (HSA) Savings Calculator—Financial Calculators from Dinktown.net. Retrieved from <www.dinktytown.net/java/SASavings.html> on Aug. 8, 2006 (3 pages).

Karkaria, Urvaksh, "Programs show patient's bill down to penny" The Florida Times-Union. Jun. 24, 2006. retrieved from <cgo.jacksonville.com/cgi-bin/printit.cgi?story=ZZNOSTORYZZ> on Apr. 5, 2007 (2 pages).

LaSalle Bank: Checking: Health Savings Account (HSA) Goal Calculator. Retrieved from <www.lasallebank.com/checking/calculators/hsa_goal.html> on Aug. 8, 2006 (2 pages).

Microsoft Press Computer Dictionary Second Edition, Microsoft Press, 1994 (p. 110).

PR Newswire. Aug. 23, 1999. Wellmed, Inc. "WellMed Introduces Industry's First Comprehensive Personal Health Management System Including Online Health Record". 3 pages.

Press Release. Feb. 22, 1999. Apelon, Inc. "WellMed and Lexical Technology Announce Joint Development Agreement for Online Consumer Health Records." 2 pages.

Quintana, Y. "User Modeling and Information Filtering for Consumer Information," New Medica Lab, IEEE, 1997. 4 pages.

Quintana, Y., Intelligent Medical Information Filtering, International Journal of Medical Informatics, 1998. 14 pages.

VisualCalc Health Savings Account Future Value Calculator. Retrieved from <www.visualcalc.com/products/calc.html> on Aug. 8, 2006 (3 pages).

"CareCalc Frequently Asked Questions and Answers," BlueCross BlueShield of Florida, (3 pages) (Jun. 2006).

* cited by examiner

SYSTEMS, DEVICES, AND METHODS FOR PROVIDING HEALTHCARE INFORMATION

CROSS-REFERENCES TO RELATED APPLICATIONS

This application claims priority to, and incorporates by reference herein in its entirety, pending U.S. Provisional Patent Application Ser. No. 60/648,821, filed 1 Feb. 2005.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DEFINITIONS

Figure 1:
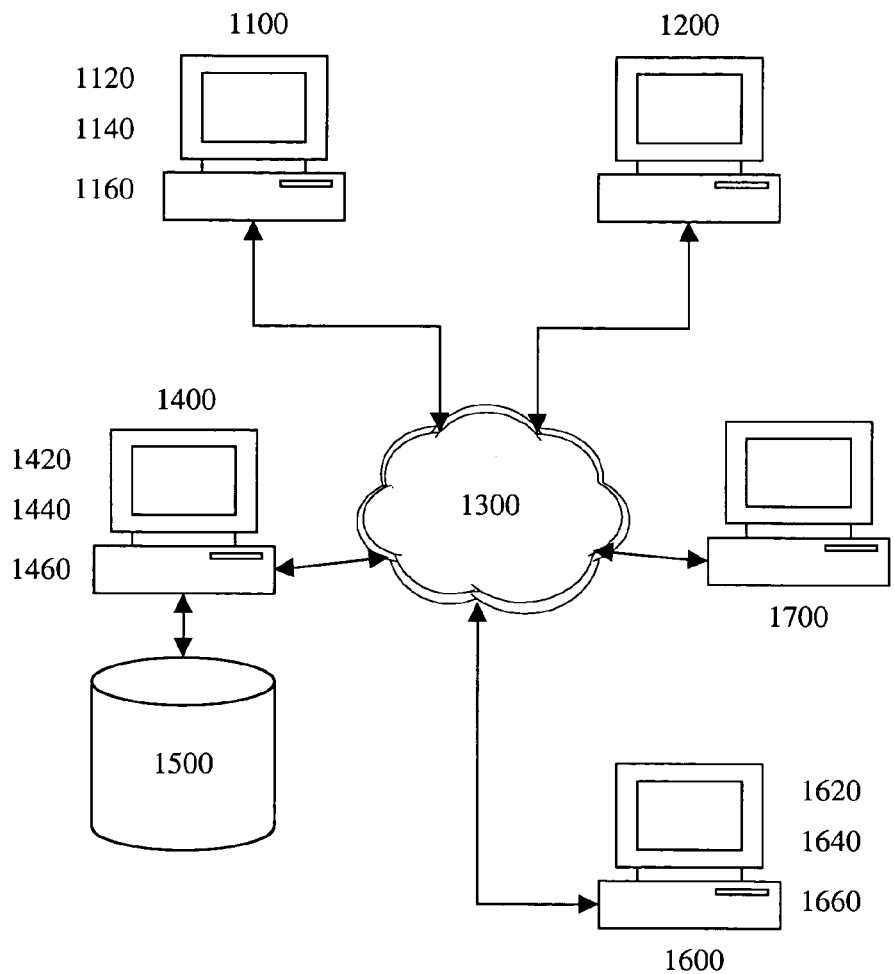
FIG. 1 is a block diagram of an exemplary embodiment of system 1000.

When the following terms are used substantively herein, the accompanying definitions apply:

a—at least one.

absolute score—a score reflecting a sum of weighted scores.

activity—an action, act, step, and/or process or portion thereof.

adapted to—made suitable or fit for a specific use or situation.

adjusted—to change and/or bring into a predetermined relationship.

and/or—either in conjunction with or in alternative to.

apparatus—an appliance or device for a particular purpose array—a matrix and/or table.

associate—to connect and/or join together; to combine.

automatically—acting or operating in a manner essentially independent of external influence or control. For example, an automatic light switch can turn on upon "seeing" a person in its view, without the person manually operating the light switch.

best matches—to correspond closer than any other.

better—higher when a scale is organized such that the highest score on that scale is the best possible score on that scale, otherwise lower.

can—is capable of, in at least some embodiments.

cause—to be the reason for, to result in, and/or to bring about.

comprising—including but not limited to.

data—distinct pieces of information, usually formatted in a special or predetermined way and/or organized to express concepts.

define—to establish the outline, form, or structure of.

determine—to ascertain, obtain, and/or calculate.

device—a machine, manufacture, and/or collection thereof.

distance—a measure of an extent of space between points on a straight line, curve, and/or road-based course.

entry—an element of an array.

facility—a building and/or place that provides a particular service and/or is used for a particular industry.

factor—a criteria and/or something that contributes to a cause of an action.

geographic region—an area on and/or near the surface of the Earth.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

healthcare—of and/or relating to the prevention, treatment, and/or management of illness and/or the preservation of mental and/or physical well-being through the services offered by the medical and/or allied health professions, including services offered by physicians, dentists, optometrists, veterinarians, physician's assistants, nurses, nutritionists, therapists, counselors, hygienists, pharmacists, opticians, healers, and/or technicians, etc.

identify—to establish the identity, origin, nature, and/or definitive characteristics of.

identity—the collective aspect of the set of characteristics by which a thing is definitively recognizable and/or known.

importance—significance and/or value.

information device—any device capable of processing information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

location—a place where something is and/or could be located.

machine instructions—directions adapted to cause a machine, such as an information device, to perform a particular operation or function.

machine readable medium—a physical structure from which a machine can obtain data and/or information. Examples include a memory, punch cards, etc.

match—to mirror, resemble, harmonize, fit, and/or correspond.

may—is allowed and/or permitted to, in at least some embodiments.

memory device—an apparatus capable of storing analog or digital information, such as instructions and/or data. Examples include a nonvolatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, ethernet card, cable modem, digital subscriber line interface, bridge, hub, router, or other similar device.

outside—the space beyond a boundary and/or limit.

packet—a discrete instance of communication.

plurality—the state of being plural and/or more than one.

predefined—specified and/or determined.

predetermined—established in advance.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

provide—to furnish, supply, give, send, and/or make available.

rank—to classify and/or to give a particular order and/or position to.

receive—to obtain, acquire, and/or take.

relate—to bring into, connect, and/or link in a logical and/or natural association.

render—make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

score—a tally and/or result, usually expressed numerically.

selectable—capable of being chosen and/or selected.

selection—the act of choosing and/or selecting and/or an assortment of things from which a choice can be made.

set—a related plurality.

statistical measure—a numerical value, such as a standard deviation and/or a mean, that characterizes the sample or population from which it was derived.

store—to place, hold, and/or retain data, typically in a memory.

substantially—to a great extent or degree.

system—a collection of mechanisms, devices, data, and/or instructions, the collection designed to perform one or more specific functions.

user—a person interfacing with an information device.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

user-selected—that which is chosen by a user.

via—by way of and/or utilizing.

weight—a factor assigned to a number in a computation to make the number's effect on the computation reflect its importance.

weighted score—a score reflecting a product of a score and a weight.

DETAILED DESCRIPTION

Described herein is a decision-support tool, sometimes referred to as the Hospital Advisor, that can allow a user to rank order the selection of resources, such as healthcare facilities. This ranking is novel and unique in that it allows the user to assign weights based on personal preferences to objectively established criteria associated with each of the healthcare facilities. In certain exemplary embodiments, the Hospital Advisor can comprise a decision-support tool designed to help users find the healthcare facility that is a best match for their needs for one or more medical procedures and/or services. The user can first express his or her preferences, or personal weightings, for each of a set of selection factors or accept the default criteria selected by a panel of medical experts. The user can also specify a geographic area and a distance (radius, driving time, etc.), which can be the outer distance limit for travel. The algorithm which implements Hospital Advisor can return a list of hospitals best meeting that set of criteria relative to the geographic area specified. In certain exemplary applications, the best match can appear as the first item in the list. Alternatively, better matches from outside the specified geographical area, for example top regional and national matches, can also be presented to give the consumer some sense of the relative scale of the comparisons. Users can learn more about any one hospital, or compare up to three hospitals at a time. The information displayed can include the number of patients receiving that procedure, various hospital characteristics, whether the hospital meets patient safety guidelines, etc. A hospital's "match score" can vary according to the preferences selected by the user. Extension of this approach to other domains within the healthcare realm (for example, selection of physicians, dentists, optometrists, therapists, counselors, professionals, aides, service providers, outpatient facilities, long-term care, home healthcare, pharmacies, laboratories, reimbursement plans, health insurance, procedures, treatments, services, medications, supplements, devices, machines, tools, software, and/or information services, etc.), and/or to other resources within and/or outside the healthcare realm, can be implemented based on the approach described herein.

In certain exemplary embodiments, the user can be offered a set of selection criteria (factors) to choose from, and can assign varying levels of importance to each. Default settings can be provided for the factors, including both whether or not the factors are selected and their importance weights. These defaults can vary by medical procedure and/or service and can be determined by medical professionals who have clinical experience and/or expertise in key and/or closely-related medical specialties.

Selection factors for users to consider and assign a preference rank can include:

Procedure Volume

Complication Score

Post-Operative Infection Score

Preference Score

JCAHO Accreditation

Teaching Status

Children's Hospital Status

Have an ICU

Have a CICU (where applicable)

Have a NICU (where applicable)

Latest Technology Available (Technology Index Score)

The preference weights can be translated in the algorithm as follows:

Not Important: weight=0

Somewhat Important: weight=⅓

Important: weight=½

Very Important: weight=1

Step one can be to determine how each hospital in the consumer's area compares to all other hospitals. This can be given as an absolute score for individual hospitals. For each selection criterion, Z-scores can be calculated by facility and by procedure within the facility. The Z-scores for procedure volume can be based on the square root of the procedure volume. This can reflect, for example, the diminishing return in learning from treating each additional patient as the number of patients treated increases. It also can reflect that modest differences in procedure volume are not as important among hospitals performing many procedures as among hospitals performing fewer procedures.

A Z-Score can be calculated as follows:

$$\frac{Score - AvScore}{StdDev}$$

where:

Score=One Hospital's Score

AvScore=Average Score For All Hospitals

StdDev=Standard Deviation of Scores For All Hospitals

Missing or insufficient data can result in a Z-score of zero. Each Z-score can be weighted by the user's preferences. The sum of weighted Z-scores can be the total hospital score.

Example: A user is searching for a hospital, and is most interested in the two factors of "Latest Technology Available", (which the user rates as "Important)", and "Neonatal ICU" status, which the user rates "Very Important".

Hospital A has the highest rating ("above average") on the "Latest Technology Available" measure. It is assigned the highest score for this factor, which is "3" (average is "2", below average is "1"). The mean (average) score for all hospitals for the technology index is 1.95, with a standard deviation of 0.59. So the Z-score for this hospital for the "technology" metric is (3-1.95)/0.59=1.78.

The score for the NICU status is calculated in a similar fashion: As it turns out, Hospital A does not have a Neonatal ICU. This is a yes/no variable—a hospital either has an NICU or it does not, so this variable is scored either "0" or "1". The mean score for NICU status is 0.21, and the standard deviation 0.41. Therefore, Hospital A has a score of (0-0.21)/0.41, or −0.51 for the NICU metric.

Step two can be that once Z-scores are calculated for each criterion and hospital, the consumer's preferences can be used to weight each Z-score, and the sum of the preference weight times the Z-score can give the hospital's absolute score.

Example: For Hospital A, the two scores for "Latest Technology Available" and "NICU status" are combined using the user's weights to get the hospital's absolute scores:
Latest Technology Z-score=1.78, Importance to user=0.5
NICU status Z-score=(−0.51), (very) Importance to user=1
Since no other factors are selected, Hospital A's absolute score is:

(0.5)*(1.78)+(1)*(−0.51)=0.38

Looking at another hospital, Hospital B: This hospital turned out to be the best match in the user's search area. It had an average score for "Latest Technology Available", with a Z-score=(2−1.95)/0.59=0.08. It also has an NICU, with a Z-score of (1−0.21)/0.41=1.79. So this hospital's absolute score is (0.5)*(0.08)+(1)*(1.79)=1.83. Thus, because 1.83 (the absolute score for Hospital B) is larger than 0.38 (the absolute score for Hospital A), Hospital B is a "better match" for the user.

Hospital C, located outside of the user's specified search radius, has both the highest score for latest technology as well as an NICU. Hospital C, then, has an absolute score of (0.5)*(1.78)+(1)*(1.79)=2.68.

Step three can be that once the absolute scores are calculated, the relative rankings of each hospital can be determined based on the geographic area defined by the consumer. To do this, each hospital can be scored as follows:

$$\frac{100*(S - WHS)}{(SRBHS - WHS)}$$

where:
S=Individual Hospital's Score
WHS=Worst Hospital's Score)
SRBHS=Search Radius's Best Hospital Score The "Worst Hospital" Score can be calculated for all of the consumer's preferences using the worst scores in the database, summed to create a theoretical "worst hospital" absolute score.

Example: Continuing with the example above, the worst hospital has no NICU and has a "below average" rating for "Latest Technology". This gives the worst hospital an absolute score of (1)*(−0.51)+(0.5)*(−1.61)=−1.32.

Next, the algorithm calculates a match score for each hospital:
Hospital A's match score is 100*(0.37−(−1.32))/(1.83−(−1.32))=54
Hospital B's match score is 100*(1.83−(−1.32))/(1.83−(−1.32))=100
Hospital C's match score is 100*(2.68−(−1.32))/(1.83−(−1.32))=127

Recall that Hospital B is the best match in the search area, and note that only hospitals outside the search are can score higher than 100.

With each hospital scored in Step 3, hospitals then can be ranked by descending match score, and/or by distance for those hospitals where match score is identical.

The algorithm can return to the user a list of hospitals best matching the criteria, with the rankings relative to other hospitals in the geographic area and to the "best match" hospitals in the region and the country.

Up to 20 matching hospitals can be included for the search area specified by the user. In the above example, the results for the user's search could include the following:

Best Match(es) in Search Area:
Hospital B score=100 distance=4 miles
Other Match(es) in Search Area:

| Hospital A score = 54 | distance = 3 miles |
| Hospital X score = 28 | distance = 2 miles |
| Hospital Y score = 28 | distance = 4 miles |

Better Match(es) Outside the Search Area:

| Hospital C score = 127 | distance = 17 miles |

Thus, certain exemplary embodiments can comprise a method that can comprise, for a predetermined user, automatically determining a score for each resource from a plurality of predetermined resources based on the user's weighting of predetermined factors associated with the resources and an objective score for each factor for each resource, ranking the scored resources, and/or providing an identity of a best matched resource for the user.

FIG. 1 is a block diagram of an exemplary embodiment of system 1000. In certain operative embodiments, system 1000 can comprise a plurality of consumer information devices 1100, 1200, which can be coupled to a network 1300. A consumer information device 1100 can comprise a user interface 1120 rendered by a client 1140 running on a browser 1160.

Also coupled to network 1300 can be a data-serving information device 1400, which can be coupled to one or more databases 1500, such as databases containing information related to specifying, rating, reviewing, comparing, evaluating, ordering, and/or obtaining a medical procedure and/or services at one or more hospitals and/or healthcare facilities. Data-serving information device 1400 can comprise an administrator and/or user interface 1420, server software 1440, and/or database management software 1460.

Also coupled to network 1300 can be one or more hospital information devices 1600 and/or one or more hospital rating service information devices 1700. A hospital information device 1600 can comprise a user interface 1620 rendered by a client 1640 running on a browser 1660.

Figure 2:
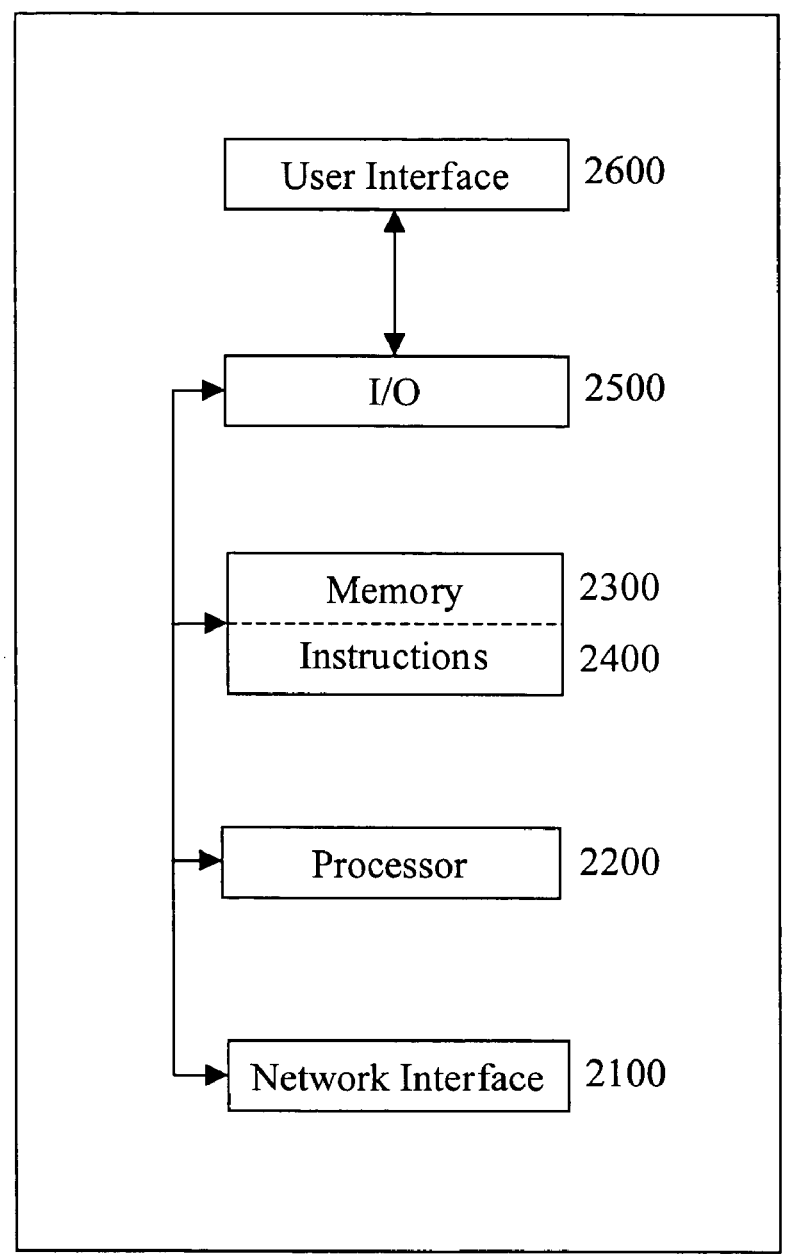
FIG. 2 is a block diagram of an exemplary embodiment of an information device 2000.

FIG. 2 is a block diagram of an exemplary embodiment of an information device 2000, which in certain operative embodiments can comprise, for example, a server, consumer information device, hospital information device, rating service information device, etc. Information device 2000 can comprise any of numerous well-known components, such as for example, one or more network interfaces 2100, one or more processors 2200, one or more memories 2300 containing instructions 2400, one or more input/output (I/O) devices 2500, and/or one or more user interfaces 2600 coupled to I/O device 2500, etc.

In certain exemplary embodiments, via one or more user interfaces 2600, such as a graphical user interface, a consumer can view a rendering of information related to specifying, rating, reviewing, comparing, evaluating, ordering, and/or obtaining a medical procedure and/or services at one or more hospitals and/or healthcare facilities.

Figure 3:
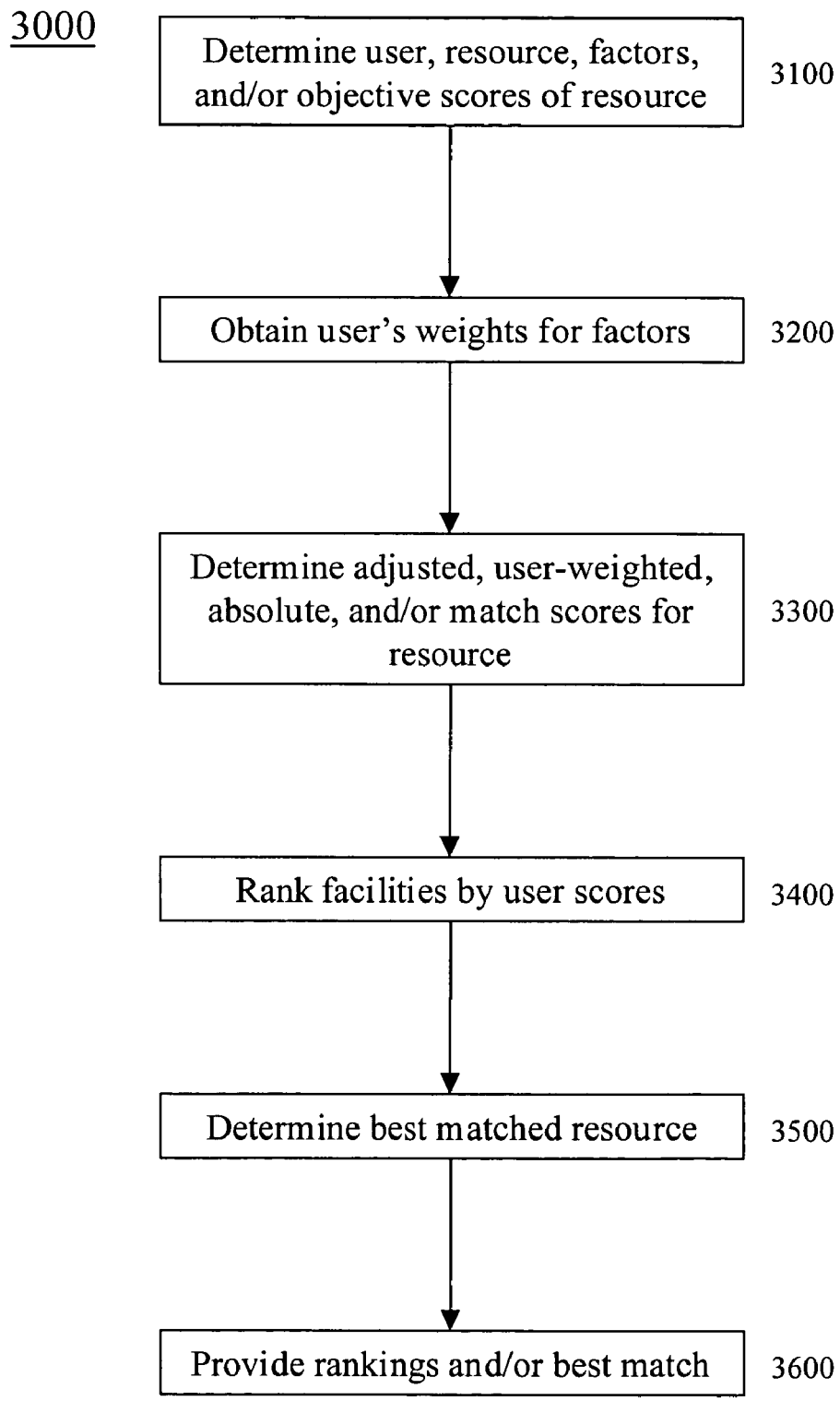
FIG. 3 is a flowchart of an exemplary embodiment of a method 3000.

FIG. 3 is a flowchart of an exemplary embodiment of a method 3000. At activity 3100, a user, resources, factors, and/or objective scores of resources can be determined. At activity 3200, user-selected weights for the factors can be obtained. At activity 3300, adjusted scores, user-weighted scores, absolute scores, and/or match scores, etc., can be obtained for the resources. At activity 3400, the resources can be ranked by adjusted scores, user-weighted scores, absolute scores, and/or match scores, etc. At activity 3500, the best matched resource for the user can be determined. At activity 3600, the rankings and/or identity of the best matched resource(s) can be provided to the user, stored, and/or reported.

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, performed by multiple entities, and/or performed in multiple jurisdictions; and any activity or element can be specifically excluded, the sequence of activities can vary, and/or the interrelationship of elements can vary.

Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A computer-implemented method comprising:
    for a predetermined user, in a computer system receiving a user-selected set of healthcare facility selection factor importance weights, each of said healthcare facility selection importance weights associated with a corresponding different healthcare facility selection factor from a set of healthcare facility selection factors;
    for each of a plurality of healthcare facilities, via the computer system automatically obtaining a healthcare facility score for each healthcare facility selection factor of the set of healthcare facility selection factors;
    for each of said plurality of healthcare facilities, via the computer system automatically determining for each healthcare facility selection factor of the set of healthcare facility selection factors an adjusted score corresponding to the healthcare facility score, each adjusted score determined from a statistical measure relating the corresponding healthcare facility score for that healthcare facility and that healthcare facility selection factor to a group healthcare facility score for that healthcare facility selection factor, said group healthcare facility score for that healthcare facility selection factor derived from the healthcare facility scores for that healthcare facility selection factor for all of said plurality of healthcare facilities;
    for each healthcare facility selection factor, via the computer system automatically, for each healthcare facility selection factor of the set of healthcare facility selection factors, determining a weighted score from said adjusted score and said associated healthcare facility selection importance weight;
    for each of said plurality of healthcare facilities, via the computer system determining an absolute score from said plurality of weighted scores; and
    via the computer system ranking the healthcare facilities among the plurality of health care facilities based on said absolute scores.

2. The method of claim 1, further comprising, for each healthcare facility selection factor from said set of healthcare facility selection factors, providing a plurality of selectable healthcare facility selection factor importance weights.

3. The method of claim 1, further comprising, determining a geographic region associated with a user.

4. The method of claim 1, further comprising, providing a set of healthcare facility selection factors to the user.

5. The method of claim 1, further comprising, determining a minimum absolute score for said plurality of healthcare facilities and a maximum absolute score for only those healthcare facilities from said plurality of healthcare facilities that are located in a predetermined geographic region.

6. The method of claim 1, further comprising, determining a minimum absolute score for said plurality of healthcare facilities and a maximum absolute score for only those healthcare facilities from said plurality of healthcare facilities that are located in a predetermined geographic region, and, for each of said healthcare facilities in the predetermined geographic region, determining a match score based on said absolute score of said healthcare facility, said minimum absolute score, and said maximum absolute score.

7. The method of claim 1, further comprising, identifying a healthcare facility from said plurality of healthcare facilities that best matches said user-selected set of healthcare facility selection factor importance weights.

8. The method of claim 1, further comprising, identifying a healthcare facility from said plurality of healthcare facilities and within a predetermined geographic region that best matches said user-selected set of healthcare facility selection factor importance weights.

9. The method of claim 1, further comprising, identifying a distance to each healthcare facility from a predefined location.

10. The method of claim 1, further comprising, identifying a healthcare facility located outside a predetermined geographic region and having a better match score than any healthcare facility within a predetermined geographic region.

11. The method of claim 1, wherein the statistical measure for each adjusted score is determined by computing a difference between the corresponding healthcare facility score and the group healthcare facility score for the corresponding healthcare facility selection factor.

12. The method of claim 1, wherein the group healthcare facility score for each of the healthcare facility selection factors is an average of the healthcare facility scores for that healthcare facility selection factor for all of said plurality of healthcare facilities.

\* \* \* \* \*